United States Patent
Fischer et al.

[11] Patent Number: 6,013,664
[45] Date of Patent: Jan. 11, 2000

[54] MICROBICIDAL AGENTS BASED ON THIOPHENE-2-CARBOXYLIC ACID DERIVATIVES

[75] Inventors: Reiner Fischer, Monheim; Norbert Lui, Köln; Stefan Dutzmann, Langenfeld; Gerd Hänssler, Leverkusen, all of Germany

[73] Assignee: Bayer Aktiengesellschaft, Leverkusen, Germany

[21] Appl. No.: 09/308,903

[22] PCT Filed: Nov. 14, 1997

[86] PCT No.: PCT/EP97/06368

§ 371 Date: May 26, 1999

§ 102(e) Date: May 26, 1999

[87] PCT Pub. No.: WO98/23605

PCT Pub. Date: Jun. 4, 1998

[30] Foreign Application Priority Data

Nov. 27, 1996 [DE] Germany .................... 196 49 093

[51] Int. Cl.$^7$ .................... A61K 31/38; A61K 31/535
[52] U.S. Cl. .................... 514/448; 514/231.5; 544/146; 549/70; 549/71; 549/72; 549/73
[58] Field of Search .................... 544/146; 549/70, 549/71, 72, 73; 514/231.5, 448

[56] References Cited

U.S. PATENT DOCUMENTS 5,484,807  1/1996  Barnes et al. .................... 514/424

FOREIGN PATENT DOCUMENTS 450355   10/1991  European Pat. Off. .
538231   4/1993   European Pat. Off. .
WO95/27397 10/1995  WIPO .

OTHER PUBLICATIONS

Arnaud, R et al Reactivity of Trifluoromethyl Erones in Michael Additions CA 123:168968, 1995.

*Primary Examiner*—Amelia Owens
*Attorney, Agent, or Firm*—Joseph C. Gil; Carol Marmo

[57] ABSTRACT

Novel microbicidal compositions based on thiophene-2-carboxylic acid derivatives, some of which are known, of the formula

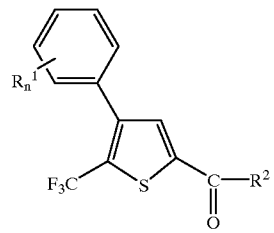

(I)

in which $R^1$, $R^2$ and n have the meanings given in the description, and the use of these substances for controlling undesired microorganisms.

Novel thiophene-2-carboxylic acid derivatives of the formula

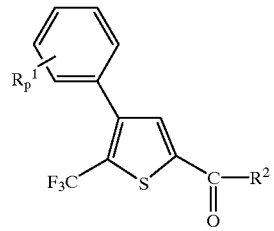

(I-a)

in which $R^1$, $R^2$ and p have the meanings given in the description, and a process for the preparation of the substances of the formula (I-a).

8 Claims, No Drawings

MICROBICIDAL AGENTS BASED ON THIOPHENE-2-CARBOXYLIC ACID DERIVATIVES

TECHNICAL FIELD OF THE INVENTION

The present invention relates to microbicidal compositions based on thiophene-2-carboxylic acid derivatives, some of which are known, and to the use of these substances for controlling undesired microorganisms. The invention furthermore also relates to new thiophene-2-carboxylic acid derivatives and to a process for their preparation.

BACKGROUND OF THE INVENTION

It has already been disclosed that certain halogen-thiophene carboxylic acid derivatives can be employed for controlling plant diseases (cf. EP-A 0 450 355 and WO 95-27 397). However, the activity of these prior-art compounds is not always satisfactory at low application rates.

Furthermore, a number of 5-trifluoromethyl-4-phenyl-thiophene-2-carboxylic esters are already known (cf. Maybridge Chemical Company, Structure List 1996). However, a microbicidal activity of these substances has not been mentioned to date.

DETAILED DESCRIPTION OF THE INVENTION

It has now been found that the thiophene-2-carboxylic acid derivatives, some of which are known, of the formula

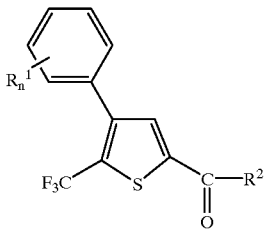

(I)

in which $R^1$ represents halogen, cyano, nitro, alkyl, halogenoalkyl, alkoxy, halogenoalkoxy, alkylthio, halogenoalkylthio, phenyl or phenoxy, n represents integers from 0 to 5 and $R^2$ represents a radical of the formula

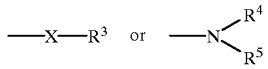

where

X represents oxygen or sulphur, $R^3$ represents hydrogen, alkyl, alkenyl, halogenoalkyl, alkoxyalkyl, pyran-4-yl, thiopyran-4-yl, optionally substituted cycloalkyl, optionally substituted cycloalkylalkyl, optionally substituted phenyl or optionally substituted phenylalkyl, and, $R^4$ and $R^5$ independently of one another represent hydrogen, alkyl, halogenoalkyl, alkoxyalkyl, alkenyl, alkinyl, alkoxycarbonylalkyl, optionally substituted cycloalkyl, optionally substituted cycloalkenyl, optionally substituted cycloalkylalkyl, optionally substituted phenyl, optionally substituted phenylalkyl or optionally substituted heterocyclyl or $R^4$ and $R^5$ together represent divalent alkanediyl having 4 to 6 carbon atoms or together represent a radical of the formula —(CH$_2$)$_2$—Y—(CH$_2$)$_2$— where Y represents oxygen, sulphur or N—$R^6$ where $R^6$ represents hydrogen, alkyl having 1 to 6 carbon atoms or benzyl, are very suitable for controlling undesired microorganism.

Surprisingly, the thiophene-2-carboxylic acid derivatives of the formula (I) which can be used in accordance with the invention have a considerably better fungicidal activity than the prior-art thiophene-carboxylic acid derivatives of the same indication which have the most similar constitution.

Formula (I) provides a general definition of the thiophene-2-carboxylic derivatives which can be used in accordance with the invention. Preferred thiophene-2-carboxylic acid derivatives of the formula (I) are those in which $R^1$ represents fluorine, chlorine, bromine, nitro, cyano, straight-chain or branched alkyl having 1 to 6 carbon atoms, halogenoalkyl having 1 to 4 carbon atoms and 1 to 5 fluorine, chlorine and/or bromine atoms, straight-chain or branched alkoxy having 1 to 6 carbon atoms, halogenoalkoxy having 1 to 4 carbon atoms and 1 to 5 fluorine, chlorine and/or bromine atoms, alkylthio having 1 to 6 carbon atoms, halogenoalkylthio having 1 to 4 carbon atoms and 1 to 5 fluorine, chlorine and/or bromine atoms, phenyl or phenoxy, n represents the numbers 0, 1, 2, 3 or 4 and $R^2$ represents a radical of the formula

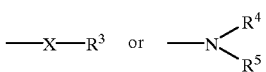

where

X represents oxygen or sulphur, $R^3$ represents hydrogen, straight-chain or branched alkyl having 1 to 6 carbon atoms, alkenyl having 2 to 6 carbon atoms, halogenoalkyl having 1 to 4 carbon atoms and 1 to 5 fluorine, chlorine and/or bromine atoms, alkoxyalkyl having 1 to 6 carbon atoms in the alkoxy moiety and 2 to 4 carbon atoms in the alkyl moiety, pyran-4-yl, thiopyran-4-yl, or cycloalkyl having 3 to 7 carbon atoms which can be monosubstituted to tetrasubstituted by identical or different substituents from the series consisting of halogen and/or alkyl having 1 to 4 carbon atoms, or $R^3$ represents cycloalkylalkyl having 3 to 7 carbon atoms in the cycloalkyl moiety and 1 to 4 carbon atoms in the alkyl moiety, it being possible for the cycloalkyl moiety to be monosubstituted to tetrasubstituted by identical or different substituents from the series consisting of halogen and/or alkyl having 1 to 4 carbon atoms, or $R^3$ represents phenyl which can be monosubstituted to trisubstituted by identical or different substituents from the series consisting of halogen, straight-chain or branched alkyl having 1 to 6 carbon atoms, straight-chain or branched alkoxy having 1 to 6 carbon atoms, halogenoalkyl having 1 or 2 carbon atoms and 1 to 5 halogen atoms and/or by halogenoalkoxy having 1 or 2 carbon atoms and 1 to 5 halogen atoms, or $R^3$ represents phenylalkyl having 1 to 4 carbon atoms in the alkyl moiety, it being possible for the phenyl moiety to be monosubstituted to trisubstituted by identical or different substituents from the series consisting of halogen, alkyl having 1 to 6 carbon atoms, alkoxy having 1 to 6 carbon atoms, halogenoalkyl having 1 or 2 carbon atoms and 1 to 5 halogen atoms and/or by halogenoalkoxy having 1 or 2 carbon atoms and 1 to 5 halogen atoms, and $R^4$ and $R^5$ independently of one another represent hydrogen, straight-chain or branched alkyl having 1 to 6 carbon atoms, halogenoalkyl having 1 to 4 carbon atoms and 1 to 5 halogen atoms, alkyloxyalkyl having 1 to 6 carbon atoms in the alkoxy moiety and 1 to 4 carbon atoms in the alkyl moiety, alkenyl having 3 to 6 carbon atoms, alkinyl having 3 to 6 carbon atoms, alkoxycarbonylalkyl having 1 to 4 carbon atoms in the alkoxy moiety and 1 to 4 carbon atoms in the alkyl moiety, or represents cycloalkyl having 3 to 8 carbon atoms, it being possible for each of the cycloalkyl radicals to be monosubstituted to tetrasubstituted by identical or different substituents from the series consisting of halogen and/or alkyl having 1 to 4 carbon atoms, or or represents cycloalkenyl having 5 to 8 carbon atoms, it being possible for each of the cycloalkenyl radicals to be monosubstituted to tetrasubstituted by identical or different substituents from the series consisting of halogen and/or alkyl having 1 to 4 carbon atoms, or represents cycloalkylalkyl having 3 to 7 carbon atoms in the cycloalkyl moiety having 1 to 4 carbon atoms in the alkyl moiety, it being possible for each of the cycloalkyl radicals to be monosubstituted to tetrasubstituted by identical or different substituents from the series consisting of halogen and/or alkyl having 1 to 4 carbon atoms, or represent phenyl which can be monosubstituted to trisubstituted by identical or different substituents from the series consisting of halogen, straight-chain or branched alkyl having 1 to 6 carbon atoms, straight-chain or branched alkoxy having 1 to 6 carbon atoms, halogenoalkyl having 1 or 2 carbon atoms and 1 to 5 halogen atoms and/or by halogenoalkoxy having 1 or 2 carbon atoms and 1 to 5 halogen atoms, or represent phenylalkyl having 1 to 4 carbon atoms in the alkyl moiety, it being possible for the phenyl moiety to be monosubstituted to trisubstituted by identical or different substituents from the series consisting of halogen, straight-chain or branched alkyl having 1 to 6 carbon atoms, straight-chain or branched alkoxy having 1 to 6 carbon atoms, halogenoalkyl having 1 or 2 carbon atoms and 1 to 5 halogen atoms and/or by halogenoalkoxy having 1 or 2 carbon atoms and 1 to 5 halogen atoms, or represents heterocyclyl having 5 or 6 ring members and 1 to 3 hetero atoms such as nitrogen, oxygen and/or sulphur, it being possible for each heterocycle to be monosubstituted or disubstituted by halogen, alkyl having 1 to 4 carbon atoms, alkoxy having 1 to 4 carbon atoms, halogenoalkyl having 1 or 2 carbon atoms and 1 to 5 halogen atoms and/or by halogenoalkoxy having 1 or 2 carbon atoms and 1 to 5 halogen atoms, or $R^4$ and $R^5$ together represent divalent alkanediyl having 4 to 6 carbon atoms or together represent a radical of the formula —$(CH_2)_2$—Y—$(CH_2)_2$— where Y represents oxygen, sulphur or N—$R^6$ where R6 represents hydrogen, alkyl having 1 to 4 carbon atoms or benzyl.

Especially preferred are those thiophene-2-carboxylic acid derivatives of the formula (I) in which $R^1$ represents fluorine, chlorine, bromine, cyano, nitro, alkyl having 1 to 4 carbon atoms, halogenoalkyl having 1 or 2 carbon atoms and 1 to 5 fluorine, and/or chlorine atoms, alkoxy having 1 to 4 carbon atoms, halogenoalkoxy having 1 or 2 carbon atoms and 1 to 5 fluorine and/or chlorine atoms, alkylthio having 1 to 4 carbon atoms, halogenoalkylthio having 1 or 2 carbon atoms and 1 to 5 fluorine and/or chlorine atoms, phenyl or phenoxy and n represents the numbers 0, 1, 2 or 3, it being possible for $R^1$ to represent identical or different radicals if n represents 2 or 3, and $R^2$ represents a radical of the formula $$—X—R^3 \quad \text{or} \quad —N\begin{matrix}R^4\\R^5\end{matrix}$$

where

X represents oxygen or sulphur, $R^3$ represents hydrogen, alkyl having 1 to 4 carbon atoms, alkenyl having 2 to 4 carbon atoms, halogenoalkyl having 1 to 4 carbon atoms and 1 to 5 fluorine, chlorine and/or bromine atoms, alkoxyalkyl having 1 to 4 carbon atoms in the alkoxy moiety and 2 or 3 carbon atoms in the alkyl moiety, pyran-4-yl, thiopyran-4-yl or cycloalkyl having 3 to 7 carbon atoms which can be monosubstituted to trisubstituted by identical or different substituents in the series consisting of fluorine, chlorine, bromine, methyl and/or ethyl, or $R^3$ represents cycloalkyl having 3 to 6 carbon atoms in the cycloalkyl moiety and 1 or 2 carbon atoms in the alkyl moiety, it being possible for the cycloalkyl moiety to be monosubstituted to trisubstituted by identical or different substituents from the series consisting of fluorine, chlorine, bromine, methyl and/or ethyl, or $R^3$ represents phenyl which can be monosubstituted to trisubstituted by identical or different substituents from the series consisting of fluorine, chlorine, bromine, alkyl having 1 to 4 carbon atoms, alkoxy having 1 to 4 carbon atoms, halogenoalkyl having 1 or 2 carbon atoms and 1 to 5 fluorine and/or chlorine atoms and/or by halogenoalkoxy having 1 or 2 carbon atoms and 1 to 5 fluorine and/or chlorine atoms, or $R^3$ represents phenylalkyl having 1 or 2 carbon atoms in the alkyl moiety, it being possible for the phenyl moiety to be monosubstituted to trisubstituted by identical or different substituents from the series consisting of fluorine, chlorine, bromine, alkyl having 1 to 4 carbon atoms, alkoxy having 1 to 4 carbon atoms, halogenoalkyl having 1 or 2 carbon atoms and 1 to 5 fluorine and/or chlorine atoms and/or by halogenoalkoxy having 1 or 2 carbon atoms and 1 to 5 fluorine and/or chlorine atoms, and $R^4$ and $R^5$ independently of one another represent hydrogen, alkyl having 1 to 4 carbon atoms, halogenoalkyl having 1 to 4 carbon atoms and 1 to 3 fluorine, chlorine and/or bromine atoms, alkoxyalkyl having 1 to 4 carbon atoms in the alkoxy moiety and 1 to 3 carbon atoms in the alkyl moiety, alkenyl having 3 to 6 carbon atoms, alkinyl having 3 to 6 carbon atoms, alkoxycarbonylalkyl having 1 or 2 carbon atoms in the alkoxy moiety and 1 or 2 carbon atoms in the alkyl moiety, or represent cycloalkyl having 3 to 7 carbon atoms, it being possible for each of the cycloalkyl radicals to be monosubstituted to tetrasubstituted by identical or different substituents from the series consisting of fluorine, chlorine, bromine, methyl and/or ethyl, or represent cycloalkenyl having 5 to 7 carbon atoms, it being possible for each of the cycloalkenyl radicals to be monosubstituted to tetrasubstituted by identical or different substituents from the series consisting of fluorine, chlorine, bromine, methyl and/or ethyl, or represent cycloalkylalkyl having 3 to 6 carbon atoms in the cycloalkyl moiety having 1 or 2 carbon atoms in the alkyl moiety, it being possible for each of the cycloalkyl radicals to be monosubstituted to tetrasubstituted by identical or different substituents from the series consisting of fluorine, chlorine, bromine, methyl and/or ethyl, or represent phenyl which can be monosubstituted to trisubstituted by identical or different substituents from the series consisting of fluorine, chlorine, bromine, alkyl having 1 to 4 carbon atoms, alkoxy having 1 to 4 carbon atoms, halogenoalkyl having 1 or 2 carbon atoms and 1 to 5 fluorine and/or chlorine atoms and/or by halogenoalkoxy having 1 or 2 carbon atoms and 1 to 5 fluorine and/or chlorine atoms, or represent phenylalkyl having 1 or 2 carbon atoms in the alkyl moiety, it being possible for the phenyl moiety to be monosubstituted to trisubstituted by identical or different substituents from the series consisting of fluorine, chlorine, bromine, alkyl having 1 to 4 carbon atoms, alkoxy having 1 to 4 carbon atoms, halogenoalkyl having 1 or 2 carbon atoms and 1 to 5 fluorine and/or chlorine atoms and/or by halogenoalkoxy having 1 or 2 carbon atoms and 1 to 5 fluorine and/or chlorine atoms, or represent heterocyclyl having 5 or 6 ring members and 1 to 3 hetero atoms such as nitrogen, oxygen and/or sulphur, it being possible for each heterocycle to be monosubstituted or disubstituted by identical or different substituents from the series consisting of fluorine, chlorine, bromine, alkyl having 1 or 2 carbon atoms, alkoxy having 1 or 2 carbon atoms, halogenoalkyl having 1 or 2 carbon atoms and 1 to 5 fluorine and/or chlorine atoms and/or by halogenoalkoxy having 1 or 2 carbon atoms and 1 to 5 fluorine and/or chlorine atoms, or $R^4$ and $R^5$ together represent divalent alkanediyl having 4 to 6 carbon atoms or together represent a radical of the formula —$(CH_2)_2$—Y—$(CH_2)_2$— where Y represents oxygen, sulphur or N—$R^6$ where $R^6$ represents hydrogen, methyl, ethyl or benzyl.

Very specially preferred are those thiophene-2-carboxylic derivatives of the formula (I) in which $R^1$ represents fluorine, chlorine, bromine, cyano, nitro, methyl, ethyl, n-propyl, isopropyl, n-butyl, sec-butyl, iso-butyl, tert-butyl, trifluoromethyl, methoxy, ethoxy, trifluoromethoxy, methylthio, trifluoromethylthio, phenyl or phenoxy, n represents the numbers 0, 1, 2 or 3, it being possible for $R^1$ to represent identical or different radicals if n represents 2 or 3, and $R^2$ represents a radical of the formula

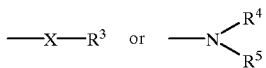

where
X represents oxygen or sulphur,
$R^3$ represents hydrogen, methyl, ethyl, n-propyl, isopropyl, n-butyl, iso-butyl, sec-butyl, tert-butyl, alkyl, 2-chloroethyl, 2,2,2-trifluoroethyl, ethoxymethyl, methoxyethyl, ethoxyethyl, pyran-4-yl, thiopyran-4-yl or represents cycloalkyl having 3 to 6 carbon atoms which can be monosubstituted or disubstituted by identical or different substituents from the series consisting of fluorine, chlorine, bromine, methyl and/or ethyl, or $R^3$ represents cycloalkylalkyl having 3 to 6 carbon atoms in the cycloalkyl moiety and 1 or 2 carbon atoms in the alkyl moiety, it being possible for the cycloalkyl moiety to be monosubstituted or disubstituted by identical or different substituents from the series consisting of fluorine, chlorine, bromine, methyl and/or ethyl, or $R^3$ represents phenyl which can be monosubstituted to trisubstituted by identical or different substituents from the series consisting of fluorine, chlorine, bromine, methyl, ethyl, isopropyl, tert-butyl, methoxy, ethoxy, trifluoromethyl and/or trifluoromethoxy, or $R^3$ represents phenylalkyl having 1 or 2 carbon atoms in the alkyl moiety, it being possible for the phenyl moiety to be monosubstituted to trisubstituted by identical or different substitutents from the series consisting of fluorine, chlorine, bromine, methyl, ethyl, isopropyl, tert-butyl, methoxy, ethoxy, trifluoromethyl and/or trifluoromethoxy, and $R^4$ and $R^5$ independently of one another represent hydrogen, methyl, ethyl, n-propyl, isopropyl, n-butyl, iso-butyl, sec-butyl, tert-butyl, 2-chloroethyl, ethoxymethyl, methoxyethyl, ethoxyethyl, allyl, propargyl, methoxycarbonylmethyl, ethoxycarbonylmethyl, methoxycarbonylethyl, ethoxycarbonylethyl or represent cycloalkyl having 3 to 6 carbon atoms, it being possible for these cycloalkyl radicals to be monosubstituted or disubstituted by identical or different substituents from the series consisting of fluorine, chlorine, bromine, methyl and/or ethyl, or represent cycloalkenyl having 5 or 6 carbon atoms, or represent cycloalkylalkyl having 3 to 6 carbon atoms in the cycloalkyl moiety and 1 or 2 carbon atoms in the alkyl moiety, it being possible for each of the cycloalkyl radicals to be monosubstituted or disubstituted by identical or different substituents from the series consisting of fluorine, chlorine, bromine, methyl and/or ethyl, or represent phenyl which can be monosubstituted or disubstituted by identical or different substituents from the series consisting of fluorine, chlorine, bromine, methyl, ethyl, isopropyl, tert-butyl, methoxy, ethoxy, trifluoromethyl and/or trifluoromethoxy, or represent phenylalkyl having 1 or 2 carbon atoms in the alkyl moiety, it being possible for the phenyl moiety to be monosubstituted or disubstituted by identical or different substituents from the series consisting of fluorine, chlorine, bromine, methyl, ethyl, isopropyl, tert-butyl, methoxy, ethoxy, trifluoromethyl and/or trifluoromethoxy, or represent furyl, tetrahydrofuryl, tetrahydropyranyl, thienyl, pyrrolyl, pyrrolidinyl, pyrazolyl, imidazolyl, thiazolyl, isothiazolyl, oxazolyl, isoxazolyl, oxadiazolyl, thiadiazolyl, pyridinyl, pyrimidinyl, pyridazinyl, pyrazinyl, 1,2,4-triazolyl, piperidinyl, morpholinyl, thiamorpholinyl or piperazinyl, it being possible for the heterocycles to be monosubstituted or disubstituted by identical or different substituents from the series consisting of fluorine, chlorine, bromine, methyl, ethyl, methoxy, ethoxy and/or trifluoromethyl, or $R^4$ and $R^5$ together represent divalent alkanediyl having 4 or 5 carbon atoms or together represent a radical of the formula —(CH$_2$)$_2$—Y—(CH$_2$)$_2$— where Y represents oxygen, sulphur or N—R$^6$ where $R^6$ represents hydrogen, methyl, ethyl or benzyl.

Some of the thiophene-2-carboxylic acid derivatives which can be used in accordance with the invention are known (cf Maybridge Chemical Company Structure List 1996).

Thiophene-2-carboxylic acid derivatives of the formula

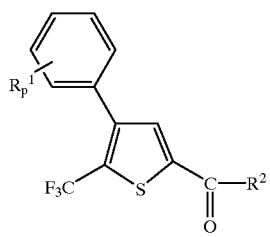

(I-a)

in which $R^1$ represents halogen, cyano, nitro, alkyl, halogenoalkyl, alkoxy, halogenoalkoxy, alkylthio, halogenoalkylthio, phenyl or phenoxy, p represents integers from 1 to 5 and $R^2$ represents a radical of the formula

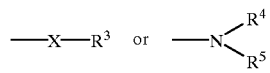

where

X represents oxygen or sulphur, $R^3$ represents hydrogen, alkyl, alkenyl, halogenoalkyl, alkoxyalkyl, pyran-4-yl, thiopyran-4-yl, optionally substituted cycloalkyl, optionally substituted cycloalkylalkyl, optionally substituted phenyl or optionally substituted phenylalkyl, and $R^4$ and $R^5$ independently of one another represent hydrogen, alkyl, halogenoalkyl, alkoxyalkyl, alkenyl, alkinyl, alkoxycarbonylalkyl, optionally substituted cycloalkyl, optionally substituted cycloalkenyl, optionally substituted cycloalkylalkyl, optionally substituted phenyl, optionally substituted phenylalkyl or optionally substituted heterocyclyl or $R^4$ and $R^5$ together represent divalent alkanediyl having 4 to 6 carbon atoms or together represent a radical of the formula —(CH$_2$)$_2$—Y—(CH$_2$)$_2$— where Y represents oxygen, sulphur or N—R$^6$ where $R^6$ represents hydrogen, alkyl having 1 to 6 carbon atoms or benzyl, are novel.

Thiophene-2-carboxylic acid derivatives. of the formula (I-a) can be prepared by reacting a) thiophene-2-carboxylic acid chloride derivatives of the formula

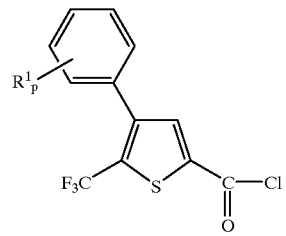

(II)

in which $R^1$ and p have the abovementioned meanings either

α) with compounds of the formula

H—X—R$^3$ (III)

in which $R^3$ and X have the abovementioned meanings, if appropriate in the presence of an acid binder and if appropriate in the presence of a diluent, or β) with amines of the formula

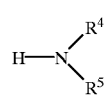

(IV)

in which $R^4$ and $R^5$ have the abovementioned meanings, if appropriate in the presence of an acid binder and if appropriate in the presence of a diluent.

The known thiophene-2-carboxylic acid derivatives of the formula (I) can be prepared analogously.

In the compounds of the formula (I-a) $R^1$ and $R^2$ preferably, or especially preferably, represent those radicals which have already been mentioned in connection with the description of the thiophene-2-carboxylic acid derivatives of the formula (I) as being preferred, or especially preferred.

If 5-trifluoromethyl-4-(4-chloro-phenyl)-thiophene-2-carboxylic acid chloride and trifluoroethanol are used as starting substances, the course of process (a, variant α) according to the invention can be illustrated by the following equation.

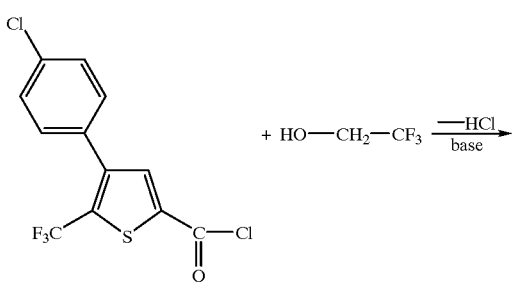 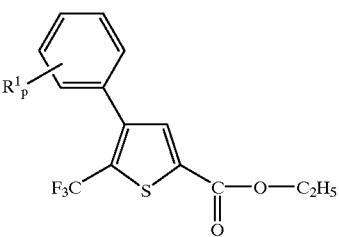

(I-b)

in which
R$^1$ and p have the abovementioned meanings
with aqueous alkali metal hydroxide solutions such as, for example, sodium hydroxide solution, in the presence of a diluent such as, for example, ethanol at temperatures between 10° C. and 80° C., then acidifying the mixture and reacting the resulting acid of the formula

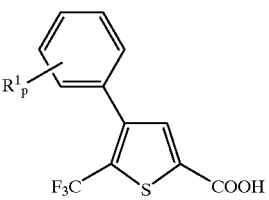

(I-c)

in which
R$^1$ and p have the abovementioned meanings
with chlorinating agents such as, for example, thionyl chloride or oxalyl chloride in the presence of a diluent such as, for example, methylene chloride at temperatures between 0° C. and 80° C.

The thiophene-2-carboxylic acid ethyl esters of the formula (I-b) which are required in the above process as starting materials can be prepared by reacting in a first step, benzyl cyanide of the formula

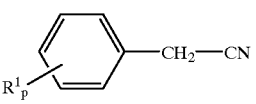

(V)

in which
R$^1$ and p have the abovementioned meanings
with ethyl trifluoroacetate, of the formula

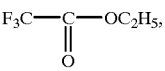

(VI)

in the presence of a strong base such as, for example, sodium ethoxide and in the presence of a diluent such as, for example, ethanol at temperatures of between 0° C. and 100° C., then, in a second step, reacting the resulting α-trifluoroacetyl-phenyl-acetonitrile derivatives of the formula If 5-trifluoromethyl-4-(4-chloro-phenyl)-thiophene-2-carboxylic acid chloride and cyclohexylamine are used as starting materials, the course of process (a, variant β) according to the invention can be illustrated by the following equation.

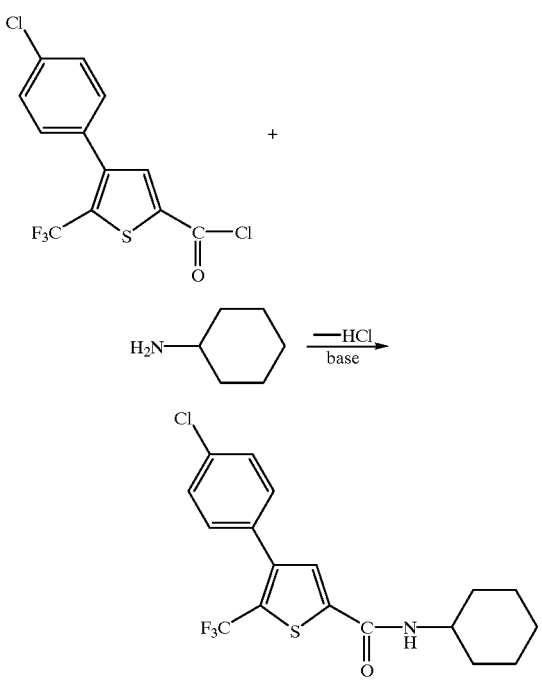

The thiophene-2-carboxylic acid chloride derivatives of the formula (II) which are required as starting materials for carrying out process (a) according to the invention are hitherto unknown. They can be prepared by reacting thiophene-2-carboxylic acid ethyl esters of the formula

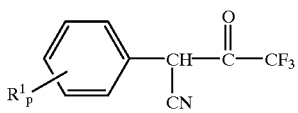

(VII)

in which
R¹ and p have the abovementioned meanings,
with sulphuric acid in the presence of water at temperatures between 120° C. and 180° C.,
in a third step, reacting the resulting phenyl-propanone derivatives of the formula

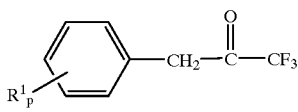

(VIII)

in which
R¹ and p have the abovementioned meanings
with phosphorus oxychloride in the presence of a diluent such as, for example, dimethyl formamide at temperatures between –10° C. and 100° C. and,
in a fourth step, reacting the resulting 2-phenyl-but-2-enal derivatives of the formula

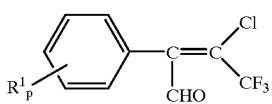

(IX)

in which
R¹ and p have the abovementioned meanings
with ethyl mercaptoacetate, of the formula

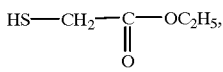

(X)

in the presence of a strong base, such as, for example, sodium hydride and in the presence of a diluent such as, for example, tetrahydrofuran, at temperatures between 0° C. and 60° C.

The compounds of the formulae (III) and (IV) which are required as reactants for carrying out process (a) according to the invention are known or can be prepared by known processes.

Suitable acid binders for carrying out process (a, variant α) according to the invention are all customary inorganic or organic bases. The following can preferably be used: the hydrides, hydroxides, amides, alkoxides, acetates, carbonates or hydrogen carbonates of alkaline earth metals or alkali metals such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium hydrogen carbonate, sodium hydrogen carbonate, furthermore ammonium hydroxide, ammonium acetate or ammonium carbonate, and also tertiary amines such as trimethylamine, N,N-dimethylaniline, pyridine, N-methylpyridine, N,N-dimethylaminopyridine, diazabicyclooctane triethylamine, (DABCO), diazabicyclononene (DBN) or diazabicycloundecane (DBU).

Suitable diluents for carrying out process (a, variant α) according to the invention are all customary inert organic solvents. The following can preferably be used: aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; nitrites such as acetonitrile, propionitrile or benzonitrile; amides such as N,N-dimethylformamide, N,N-dimethylacetamide, N-methylformanilide, N-methylpyrrolidone or hexamethyl phosphoric triamide, or sulfoxides such as dimethyl sulfoxide.

Process (a, variant α) according to the invention is also carried out in the presence of a suitable catalyst, if appropriate. Suitable catalysts are, in particular, copper-(I) salts such as, for example, copper(I) chloride. An addition of catalytic amounts of a suitable phase transfer catalyst such as, for example, 15-Krone-5, 18-Krone-6 or tris-[2-(2-methoxyethoxy)-ethyl]-amine may be advantageous.

When carrying out process (a, variant α) according to the invention, the reaction temperatures can be varied within a substantial range. In general, this is done at temperatures between –20° C. and +180° C., preferably at temperatures between 0° C. and +150° C.

Process (a) according to the invention is generally carried out under atmospheric pressure.

When carrying out process (a, variant α) according to the invention, 1.0 to 3.0 mol or else a larger excess of compound of the formula (III) and 1.0 to 3.0 mol of base are generally employed per mol of thiophene-2-carboxylic acid chloride derivative of the formula (II). Working-up is carried out by customary methods.

Suitable acid binders for carrying out process (a, variant β) according to the invention are all customary inorganic or organic bases. The following can preferably be used: the hydrides, hydroxides, amides, alkoxides, acetates, carbonates or hydrogen carbonates of alkaline earth metals or alkali metals such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium hydrogen carbonate, sodium hydrogen carbonate, furthermore ammonium hydroxide, ammonium acetate or ammonium carbonate, and also tertiary amines such as trimethylamine, triethylamine, tributylamine, N,N-dimethylaniline, pyridine, N-methylpyridine, N,N-dimethylaminopyridine, diazabicyclooctane (DABCO), diazabicyclononene (DBN) or diazabicycloundecane (DBU).

Suitable diluents for carrying out process (a, variant β) according to the invention are all customary inert organic solvents. The following can preferably be used: aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether, ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethyl phosphoric triamide; esters such as methyl acetate or ethyl acetate, or sulfoxides such as dimethyl sulfoxide.

If appropriate, process (a, variant β) according to the invention can also be carried out in a two-phase system such as, for example, water/toluene or water/dichloromethane, if appropriate in the presence of a suitable phase transfer catalyst. The following may be mentioned as examples of such catalysts: tetrabutylammonium iodide, tetrabutyl ammonium bromide, tetrabutyl ammonium chloride, tributyl methyl phosphonium bromide, trimethyl-$C_{13}/C_{15}$-alkylammonium chloride, trimethyl-$C_{13}/C_{15}$-alkylammonium bromide, dibenzyl-dimethyl-ammonium methylsulfate, dimethyl-$C_{12}/C_{14}$-alkylbenzylammonium chloride, dimethyl-$C_{12}/C_{14}$-alkyl-benzyl-ammonium bromide, tetrabutylammonium hydroxide, triethylbenzylammonium chloride, methyltrioctylammonium chloride, trimethylbenzylammonium chloride, 15-Krone-5, 18-Krone-6 or tris-[2-(2-methoxyethoxy)-ethyl]-amine.

When carrying out process (a, variant β) the reaction temperatures can be varied within a substantial range. It is generally done at temperatures between −20° C. and 150° C., preferably at temperatures between 0° C. and 120° C.

When carrying out process (a, variant β) according to the invention, 1 to 5 mol of amine of the formula (IV) and, if appropriate 1 to 5 mol of acid binder are generally employed per mol of thiophene-2-carboxylic acid chloride derivative of the formula (II). Working-up is carried out by customary methods.

The substances which can be used in accordance with the invention have a powerful microbicidal activity and can be used for controlling undesired microorganisms such as fungi and bacteria in crop protection and in the protection of material. Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Psdeudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidial form: Drechslera, syn: Helminthosporium);
Cochliobolus species, such as, for example, *Cochliobolus sativus* (conidial form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Scierotinia sclerotiorum;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The good plant tolerance of the active compounds, at the concentrations required for controlling plant diseases, permits the treatment of aerial parts of the plants, propagation and seed, and of the soil.

The active compounds which can be used in accordance with the invention can be employed particularly successfully for controlling diseases in viticulture, fruit and vegetable production such as, for example, against Phytophthora species. They also provide good control of cereal diseases such as, for example, Erysiphe species, or rice diseases such as, for example, Pyricularia species. The compounds which can be used in accordance with the invention can furthermore also be employed for increasing the yield of crop plants.

In the protection of materials, the substances which can be used in accordance with the invention can be employed for protecting industrial materials against infection with and destruction by, undesirable microorganisms.

Industrial materials in the present context are to be understood as meaning non-live materials which have been prepared for use in industry. For example, industrial materials which are intended to be protected by active compounds according to the invention from microbial change or destruction can be glues, sizes, paper and board, textiles, leather, wood, paints and synthetic articles, cooling lubricants and other materials which can be infected with, or destroyed by, microorganisms. Parts of production plants, for example, cooling-water circuits, which may be impaired by the multiplication of microorganisms may also be mentioned within the scope of the materials to be protected. Industrial materials which may be mentioned within the scope of the present invention are preferably glues, sizes, paper and board, leather, wood, paints, cooling lubricants and heat-transfer liquids.

Examples of microorganisms which are capable of bringing about degradation of, or change in, the industrial materials and which may be mentioned are bacteria, fungi, yeasts, algae and slime organisms. The active compounds or compositions according to the invention preferably act against fungi, in particular moulds, and against slime organisms and algae.

Microorganisms of the following genera may be mentioned by way of example:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Depending on the particular physical and/or chemical properties, the active compounds can be converted into customary formulations, such as solutions, emulsions, suspensions, powders, foams, pastes, granules, aerosols and microencapsulations in polymeric substances and in coating compositions for seed, and ULV cold and hot fogging formulations.

These formulations are produced in a known manner, for example by mixing the active compounds with extenders, that is, liquid solvents, liquefied gases under pressure, and/or solid carriers, optionally with the use of surfactants, that is, emulsifiers, and/or dispersants and/or foam formers. In the case of their use of water as an extender, organic solvent can, for example, also be used as auxiliary solvents. The following are mainly suitable as liquid solvents: aromatics such as xylene, toluene, alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at ambient temperature and under atmospheric pressure, for example aerosol propellants such as halogenohydrocarbons or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly-dispersed silica, alumina and silicates. Suitable solid carriers for granules are: for example crushed and fractionated natural rocks such as calcite, marble, pumice, sepiolite and dolamite, or else synthetic granules of inorganic and organic meals, and granules of organic material such as sawdust, coconut shells, maize cobs and tobacco stalks. Suitable emulsifiers and/or foam formers are: for example non-ionic and anionic emulsifiers such as polyoxyethylene fatty acid esters, polyoxyethylene fatty alcohol ethers, for example alkylaryl polyglycol ethers, alkyl sulfonates, alkyl sulfates, aryl sulfonates, or else protein hydrolysates. Suitable dispersants are: for example lignin-sulfite waste liquors and methyl cellulose.

Adhesives such as carboxymethylcellulose and natural and synthetic polymers in the form of powders, granules or lattices, such as gum arabic, polyvinyl alcohol, polyvinyl acetate or else natural phospholipids such as cephalines and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanin dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds which can be used in accordance with the invention, as such or in their formulations, can also be used as a mixture with known fungicides, bactericides, acaricides and nematicides or insecticides, for example to widen the spectrum of action or to prevent the development of resistance. In many cases, synergistic effects are obtained, that is, the activity of the mixture is greater than the activity of the individual components.

Examples of suitable components in mixtures are the following:
Fungicides:
Aldimorph, ampropylfos, ampropylfos-potassium, andoprim, anilazin, azaconazole, azoxystrobin,
benalaxyl, benodanil, benomyl, benzamacril, Benzamacryl-isobutyl, bialaphos, binapacryl, biphenyl, bitertanol, blasticidin-S, bromuconazole, bupirimate, buthiobate,
calcium polysulfide, capsimycin, captafol, captan, carbendazim, carboxin, carvon, chinomethionate (quinomethionate), chlorbenthiazone, chlorfenazole, chloroneb, chlioropicrin, chlorothalonil, chlozolinate, clozylacon, cufraneb, cymoxanil, cyproconazole, cyprodinil, cyprofuram,
debacarb, dichlorophen, diclobutrazol, diclofluanid, diclomezin, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
ediphenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromid, fluquinconazole, flurprimidol, flusilazole, flusulfamide, flutolanil, flutriafol, folpet, fosetyl-alminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadinealbesilate, iminoctadinetriacetate, iodocarb, ipconazole, iprobenfosufen(IBP), iprodione, irumamycin, isoprothiolane, isovaledione,
kasugamycin, kresoxim-methyl, copper preparations such as: copper hydroxide, copper naphthenate, copper oxychloride, copper sulfate, copper oxide, oxine-copper and Boerdeaux mixture,
mancopper, mancozeb, maneb, meferimzone, mepanipyrim, mepronil, metalaxyl, metconazole methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinicacid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, popamocarb, propanosine-sodium, propiconazole, propineb, pyrazophos, pyrifenox, pyrimethanil, pyroquilon, pyroxyfur,
quinconazole, quintozene(PCNB),
sulphur and sulphur preparations,
tebuconazol, tecloftalarn, technazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutanil, triazoxide, trichlamide, tricyclazole, tridemorph, triflumizol, triforine, triticonazole,
uniconazole,
validamycin A, vinclozolin, viniconazole,
zarilamid, zineb, ziram or else
Dagger G,
OK-8705,
OK-8801,
α-(1,1-dimethylethyl)-β-(2-phenoxyethyl)-1H-1,2,4-triazol-1-ethanol,
α-(2,4-dichlorophenyl)-β-fluoro-β-propyl-1H-1,2,4-triazol-1-ethanol,
α-(2,4-dichlorophenyl)-β-methoxy-a-methyl-1H-1,2,4-triazol-1-ethanol,
α-(5-methyl-1,3-dioxan-5-yl)-β-[[4-(trifluoromethyl)-phenyl]-methylene]1H-1,2,4-triazol-1-ethanol,
(5RS,6RS)-6-hydroxy-2,2,7,7-tetramethyl-5-(1H1,2,4-triazol-1-yl)-3-octanone,
(E)-α(methoxyimino)-N-methyl-2-phenoxy-phenylacetamide,
{2-methyl-1-[[[1-(4-methylphenyl)-ethyl]-amino]-carbonyl]-propyl}-carbamate-1-isopropyl ester
1-(2,4-dichlorophenyl)-2-(1H-1,2,4-triazol-1-yl)ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidinedione,
1-[(diiodomethyl)-sulfonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoro-methyl-1,3-thiazole-5-carboxanilide,
2,2-dichloro-N-[1-(4-chlorophenyl)-ethyl]-1-ethyl-3-methyl-cyclopropane carboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulfonyl]-5-(trichloromethyl)-1,3,4-thiadiazole,
2-[[6-deoxy-.4-.O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentandinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol(OPP),
3,4-dichloro-1-[4-(difluoromethoxy)-phenyl]-1H-pyrrole-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4chloro-2-cyano-N,N-dimethyl-5-(4-methylphenyl)-1H-imidazole-1-sulfonamide,
4-methyl-tetrazolo[1,5-a]quinazolin-5(4H)-onm,
8-(1,1-dimethylethyl)-N-ethyl-N-propyl-1,4-dioxaspiro[4.5]decane-2-methanamine,
8-hydroxyquinolinsulfate,
N-2-[(phenylamino)-carbonyl]-9H-xanthene-9-carbohydrazine,
bis-(1-methylethyl)-3-methyl-4-[(3-methylbenzoyl)oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium hydrogen carbonate,
sodium methane tetrathiolate
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloracetyl)-N-(2,6-dimethylphenyl)-DL-alaninate,
N-(2,3-dichloro-4-hydroxyphenyl)-1-methyl-cyclohexane carboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzene sulfonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-.oxo-3-oxazolidinyl)-acetamide,
N-(6-methoxy)-3-pyridinyl)-cyclopropanecarboxamide,
N-[2,2,2-trichloro-1-[(chloracetyl)-amino]-ethyl]-benzamide,
N-[3-chloro-4,5-bis(2-propinyloxy)-phenyl]-N'-methoxy-methanimidaride,
monosodium N-formyl-N-hydroxy-DL-alaninate
O,O-diethyl [2-(dipropylamino)-2-oxoethyl]-ethylphosphoramidothioate,
O-methyl S-phenyl phenylpropylphosphoramidothioate,
S-methyl1,2,3-benzothiadiazole-7-carbothioate,
spiro[2H]-1-benzopyran-2,1'(3'H)-isobenzofuran]-3'-one,
Bactericides:
bromopol, dichlorophen, nitrapyrin, nickel dimethyldithiocarbamate, kasugamycin, octhilinone, furan-carboxylic acid, oxytetracyclin, probenazole, streptomycin, tecloftalam, copper sulfate and other copper preparations.
Insecticides/acaricides/nematicides:
abamectin, acephate, acrinathrin, alanycarb, aldicarb, alphamethrin, amitraz, avermectin, AZ 60541, azadirachtin, azinphos A, azinphos M, azocyclotin,
Bacillus thuringiensis, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano- N-methyl-ethanimidamide, chlorpyrifos, chlorpyrifos M, cis-resmethrin, clocythrin, clofentezin, cyanophos, cycloprothrin, cyfluthrin, cyhalothrin, cyhexatin, cypermethrin, cyromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinat, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, nitenpyram omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenophos, promecarb, propaphos, propoxur, prothiophos, prothoat, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds such as herbicides or with fertilizers and growth regulators is also possible.

The active compounds can be used as such, in the form of their commercially available formations or the use forms prepared therefrom, such as ready-to-use solutions, suspensions, wettable powders, pastes, soluble powders, dusts and granules. They are used in the customary manner, for example by pouring, spraying, atomizing, scattering, foaming, brushing on and the like. It is furthermore possible to apply the active compounds by the ultra-low volume method, or to inject the active compound formulation or the active compound itself into the soil. The seed of the plant can also be treated.

For the treatment of parts of plants, the concentration of active compound in the use forms can be varied within a substantial range. They are generally between 1 and 0.0001% by weight, preferably between 0.5 and 0.001% by weight.

For the treatment of seeds, amounts of 0.001 to 50 g of active compound are generally required per kilogram of seed, preferably 0.01 to 10 g.

For the treatment of the soil, active compound concentrations of 0.00001 to 0.1% by weight, preferably 0.0001 to 0.02% by weight, are required at the site of action.

The compositions used for the protection of industrial materials generally comprise the active compounds in an amount of 1 to 95%, preferably 10 to 75%.

The use concentrations of the active compound which can be used in accordance with the invention depend on the species and the occurrence of the micoorganisms to be controlled and on the composition of the material to be protected. The optimum rate can be determined by test series. In general, the use concentrations are in the range of 0.001 to 5% by weight, preferably 0.05 to 1.0% by weight, based on the material to be protected.

The preparation and the use of active compounds according to the invention are illustrated by the examples which follow.

PREPARATION EXAMPLES

EXAMPLE 1

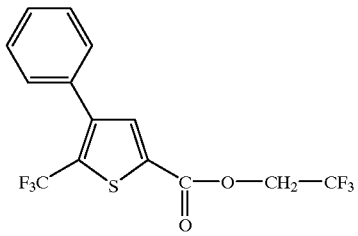

(I-1)

A mixture of 2.5 g (8.6 mmol) of 5-trifluoromethyl-4-phenyl-thiophene-2-carboxylic acid chloride and 30 ml of methylene chloride is treated at room temperature with 1.5 g (15 mmol) of 2,2,2-trifluoroethanol and 1.0 g (10 mmol) triethylamine, with stirring. The reaction mixture is stirred for 2 hours at room temperature and then poured into water. The organic phase is separated off and the aqueous phase is extracted with methylene chloride. The combined organic phases are washed in succession with dilute aqueous hydrochloric acid and with water. After drying over sodium sulfate, the organic phase is concentrated under reduced pressure. The residue which remains is chromatographed over silica gel. This gives 2,2,2-trifluoroethyl 5-trifluoromethyl-4-phenyl-thiophene-2-carboxylate.

$^1$H-NMR-spectrum (CDCl$_3$/TMS): δ=4.71 (q,2H); 7.43 (s,1H); 7.83 (s,1H) ppm

Preparation of Starting Materials

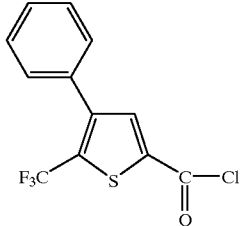

(II-1)

22.8 g of oxalyl chloride are added dropwise with stirring at room temperature to a mixture of 44 g (0.16 mol) of 5-trifluoromethyl-4-phenyl-thiophene-2-carboxylic acid, 0.5 g of dimethylformamide and 250 ml of methylene chloride. The reaction mixture is stirred until the evolution of gas has ceased and then concentrated under reduced pressure. This gives 47 g of 5-trifluoromethyl-4-phenyl-thiophene-2-carboxylic acid chloride.

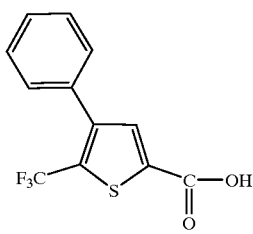

(I-2)

320 ml of 1N aqueous sodium hydroxide solution are added dropwise at room temperature with stirring to a solution of 58 g of ethyl 5-trifluoromethyl-4-phenyl-thiophene-2-carboxylate in 100 ml of ethanol. The reaction mixture is stirred for 12 hours at room temperature and then brought to pH 1 with diluted hydrochloric acid. The mixture is concentrated under reduced pressure, the residue which remains is extracted with methylene chloride, and the organic phase is dried over sodium sulfate and concentrated under reduced pressure. This gives 44 g of 5-trifluoromethyl-4-phenyl-thiophene-2-carboxylic acid.

m.p.: 115° C. (comp.)

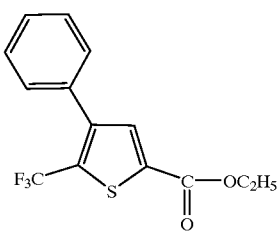

(I-3)

First, 28.8 g (0.24 mol) of ethyl mercaptoacetate and then a solution of 48 g (0.2 mol) of 3-chloro-4,4,4-trifluoro-2-phenyl-but-2-enal in 60 ml of tetrahydrofuran are added dropwise at room temperature with stirring under nitrogen atmosphere to a mixture of 400 ml of tetrahydrofuran and 9.6 g (0.24 mol) of sodium hydride (60% in mineral oil). When the addition has ended, the reaction mixture is stirred at room temperature for a further 6 hours and then poured into water. It is extracted repeatedly with methylene chloride and the combined organic phases are dried over sodium sulfate. After concentration under reduced pressure, 58 g of ethyl-5-trifluoromethyl-4-phenyl-thiophene-2-carboxylate remains.

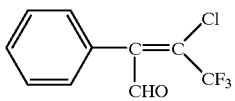

(IX-1)

375 ml of dimethylformamide are added dropwise at 0° C. with stirring in the course of 2 hours to 210 ml (2.25 mol) of phosphorus oxychloride. Stirring is continued for 30 minutes, and 141 g (0.75 mol) of 1,1,1-trifluoro-3-phenyl-propan-2-one are then added dropwise with stirring at room temperature. The reaction mixture is stirred for 5 hours at 65° C. and subsequently poured into iced water. The mixture is treated with 500 ml of saturated aqueous sodium acetate solution, stirred for 2 hours at room temperature and extracted repeatedly with methylene chloride. The combined organic phases are washed with saturated aqueous sodium hydrogen carbonate solution and then dried over sodium sulfate. The mixture is concentrated under reduced pressure, and the residue which remains is warmed to 40° C. under a pressure of I mbar. This gives 161 g of 3-chloro-4,4,4-trifluoro-2-phenyl-but-2-enal.

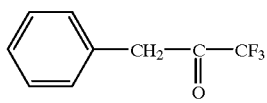

(VIII-1)

140 g (0.74 mol) of α-trifluoroacetylphenylacetonitrile are added at room temperature with stirring to a mixture of 235 ml of water and 390 g of concentrated sulphuric acid. The reaction mixture is stirred for 18 hours at 140 to 150° C. 400 ml of water are subsequently added dropwise at a bath temperature of 190° C. At the same time, the volatile components are distilled off at this temperature. The organic phase is dried over sodium sulfate. This gives 90 g of 1,1,1-trifluoro-3-phenyl-propan-2-one.

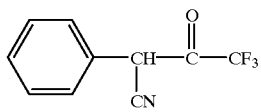

(VII-1)

A mixture of 213 g (1.5 mol) of ethyl trifluoroacetate and 175 g (1.5 mol) of benzyl cyanide is added dropwise at room temperature with stirring to 510 g (1.5 mol) of a 20% strength solution of sodium ethoxide in ethanol. The reaction mixture is refluxed for 16 hours, left to cool, poured into ice-water and treated with 150 ml of aqueous hydrochloric acid. The resulting mixture is extracted repeatedly with methyl tert-butyl ether. The combined organic phases are dried over sodium sulfate and then concentrated under reduced pressure. This gives α-trifluoroacetyl-phenyl-acetonitrile.

The thiophene-2-carboxylic acid derivatives of the formula

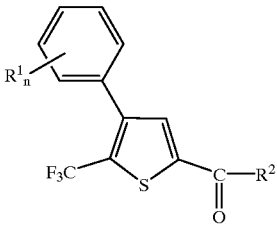

(I)

shown in the table which follows are also obtained by the above-described methods.

TABLE 1

| Ex. No. | Comp. No. | $R_n^1$ | $R^2$ | Physical data |
|---|---|---|---|---|
| 2 | I-4 | — | —O—CH₂—C₆H₅ | δ = 5.37(s, 2H); 7.4(m, 10H); 7.77 (s, 1H) ppm |
| 3 | I-5 | — | —O—(CH₂)₂—O—CH₃ | δ = 3.44(s, 3H); 3.72(m, 2H); 4.49 (m, 2H); 7.43 (s, 5H); 7.78 (s, 1H) ppm |
| 4 | I-6 | — | —O—(4-F-C₆H₄) | δ = 7.12(m, 2H); 7.12(m, 2H); 7.45 (s, 5H); 7.92 (s, 1H) ppm |
| 5 | I-7 | — | —N(CH₃)₂ | m.p. = 63° C. |
| 6 | I-8 | — | —NH₂ | m.p. = 177° C. |
| 7 | I-9 | — | —NH—CH₃ | m.p. = 153° C. |
| 8 | I-10 | — | —NH—(CH₂)₂—OCH₃ | mp. = 86° C. |
| 9 | I-11 | — | —NH—(CH₂)₂—(3,4-di-OCH₃-C₆H₃) | m.p. = 115° C. |
| 10 | I-12 | — | —NH—CH₂—C(=O)—OCH₃ | m.p. 112° C. |
| 11 | I-13 | — | —NH—cyclohexyl | m.p. 158° C. |
| 12 | I-14 | 4-Cl | —O—C₂H₅ | oil |
| 13 | I-15 | 4-Cl | —OH | |
| 14 | I-16 | — | —OCH₃ | oil |
| 15 | I-17 | — | —O—(2,4-di-Cl-C₆H₃) | oil |
| 16 | I-18 | — | —NH—C(CH₃)₃ | |
| 17 | I-19 | — | —NH—(2,4-di-Cl-C₆H₃) | oil |
| 18 | I-20 | — | —NH—(4-Cl-C₆H₄) | |

TABLE 1-continued

| Ex. No. | Comp. No. | $R_n^1$ | $R^2$ | Physical data |
|---|---|---|---|---|
| 19 | I-21 | — | —NH—(3-amino-5-methylisoxazolyl) | |
| 20 | I-22 | — | —O—CH(CH$_3$)$_2$ | oil |
| 21 | I-23 | — | —O—C(CH$_3$)$_3$ | oil |
| 22 | I-24 | — | —O—CH$_2$—CH=CH$_2$ | oil |
| 23 | I-25 | — | —O—cyclohexyl | oil |
| 24 | I-26 | — | —O—CH$_2$—cyclohexyl | oil |
| 25 | I-27 | 4-Cl | —NH$_2$ | m.p. 150° C. |
| 26 | I-28 | 4-Cl | —N(CH$_3$)$_2$ | crystalline wax |
| 27 | I-29 | 4-Cl | —NH—cyclohexyl | m.p. 120° C. |
| 28 | I-30 | 4-Cl | —O—CH(CH$_3$)$_2$ | oil |
| 29 | I-31 | 4-Cl | —OCH$_3$ | oil |
| 30 | I-32 | 4-Cl | —O—CH$_2$—CH=CH$_2$ | oil |
| 31 | I-33 | 4-Cl | —O—(4-fluorophenyl) | oil |
| 32 | I-34 | 4-Cl | —O—cyclohexyl | oil |
| 33 | I-35 | 4-Cl | —O—CH$_2$—CF$_3$ | oil |
| 34 | I-36 | 4-Cl | —O—CH$_2$—phenyl | oil |
| 35 | I-37 | 4-Cl | —O—CH$_2$—cyclohexyl | oil |
| 36 | I-38 | 4-Cl | —O—(CH$_2$)$_2$—O—CH$_3$ | oil |
| 37 | I-39 | 2,4-Cl$_2$ | —O—C$_2$H$_5$ | oil |
| 38 | I-40 | 3,4-Cl$_2$ | —O—C$_2$H$_5$ | oil |
| 39 | I-41 | 3,4-Cl | —OH | m.p.: 131° C. |
| 40 | I-42 | — | —NH—CH$_2$—CH=CH$_2$ | m.p. 108° C. |
| 41 | I-43 | — | —morpholino | oil |
| 42 | I-44 | 2,4-Cl$_2$ | —NH—CH$_2$—COO—CH$_3$ | oil |
| 43 | I-45 | 4-Cl | —NH—CH$_3$ | |

TABLE 1-continued

| Ex. No. | Comp. No. | $R_n^1$ | $R^2$ | Physical data |
|---|---|---|---|---|
| 44 | I-46 | 4-Cl | —NH—(CH$_2$)$_2$—O—CH$_3$ | m.p. 79° C. |
| 45 | I-47 | 4-Cl | —NH—(2,4-dichlorophenyl) | oil |
| 46 | I-48 | 4-Cl | —NH—(CH$_2$)$_2$—(3,4-dimethoxyphenyl) | wax |
| 47 | I-49 | 4-Cl | —NH—CH$_2$COO—CH$_3$ | oil |
| 48 | I-50 | 4-Cl | morpholin-4-yl | oil |
| 49 | I-51 | 2,4-Cl$_2$ | —O—CH(CH$_3$)$_2$ | oil |
| 50 | I-52 | 2,4-Cl$_2$ | —OCH$_3$ | oil |
| 51 | I-53 | 2,4-Cl$_2$ | —O—CH$_2$—CH=CH$_2$ | oil |
| 52 | I-54 | 2,4-Cl$_2$ | —O—(4-fluorophenyl) | oil |
| 53 | I-55 | 2,4-Cl$_2$ | —O—cyclohexyl | oil |
| 54 | I-56 | 2,4-Cl$_2$ | —O—CH$_2$—CF$_3$ | oil |
| 55 | I-57 | 2,4-Cl$_2$ | —O—CH$_2$—phenyl | oil |
| 56 | I-58 | 2,4-Cl$_2$ | —O—CH$_2$—cyclohexyl | oil |
| 57 | I-59 | 2,4-Cl$_2$ | —O—(CH$_2$)$_2$—OCH$_3$ | oil |
| 58 | I-60 | 3,4-Cl$_2$ | —O—CH(CH$_3$)$_2$ | oil |
| 59 | I-61 | 3,4-Cl$_2$ | —OCH$_3$ | oil |
| 60 | I-62 | 3,4-Cl$_2$ | —O—CH$_2$—CH=CH$_2$ | oil |
| 61 | I-63 | 3,4-Cl$_2$ | —O—(4-fluorophenyl) | oil |
| 62 | I-64 | 3,4-Cl$_2$ | —O—cyclohexyl | oil |
| 63 | I-65 | 3,4-Cl$_2$ | —O—CH$_2$—CF$_3$ | oil |

TABLE 1-continued

| Ex. No. | Comp. No. | $R_n^1$ | $R^2$ | Physical data |
|---|---|---|---|---|
| 64 | I-66 | 3,4-Cl$_2$ | —O—CH$_2$—C$_6$H$_5$ (phenyl) | oil |
| 65 | I-67 | 3,4-Cl$_2$ | —O—CH$_2$—C$_6$H$_{11}$ (cyclohexyl) | oil |
| 66 | I-68 | 3,4-Cl$_2$ | —O—(CH$_2$)$_2$—O—CH$_3$ | oil |
| 67 | I-69 | 2,4-Cl$_2$ | —NH$_2$ | |
| 68 | I-70 | 2,4-Cl$_2$ | —NH—C$_6$H$_{11}$ (cyclohexyl) | m.p. 171° C. |
| 69 | I-71 | 2,4-Cl$_2$ | —NH—(CH$_2$)$_2$—OCH$_3$ | m.p. 104° C. |
| 70 | I-72 | 2,4-Cl$_2$ | —NH—(CH$_2$)$_2$—(3,4-dimethoxyphenyl) | m.p. 103° C. |
| 71 | I-73 | 2,4-Cl$_2$ | —NH—CH$_2$—COO—CH$_3$ | oil |
| 72 | I-74 | 3,4-Cl$_2$ | —NH$_2$ | m.p. 159° C. |
| 73 | I-75 | 3,4-Cl$_2$ | —NH—C$_6$H$_{11}$ (cyclohexyl) | m.p. 114° C. |
| 74 | I-76 | 3,4-Cl$_2$ | —NH—CH$_2$—COO—CH$_3$ | oil |

USE EXAMPLES

Example A

Erysiphe-Test (barley)/protective

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. hordei.

The plants are placed in a greenhouse at a temperature of approx. 20° C. and a relative atmospheric humidity of approx. 80% to promote the development of mildew pustules.

The test is evaluated 7 days after inoculation. 0% means an efficacy which corresponds to that of the untreated control, while an efficacy of 100% means that no disease is observed.

Active compounds, application rates and test results can be seen from the table which follows.

TABLE A
Erysiphe-Test (barley)/protective
| Active compound | Application rate of active compound in g/ha | Efficacy in % |
|---|---|---|
| According to the invention | | |
| 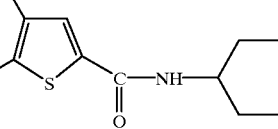<br>(I-13) | 250 | 63 |
| 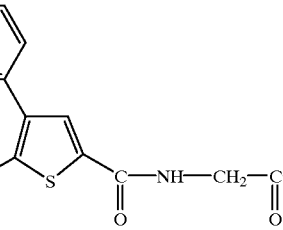<br>(I-12) | 250 | 63 |
| 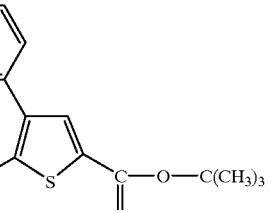<br>(I-23) | 250 | 63 |
| 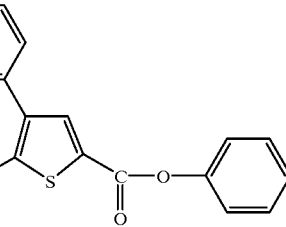<br>(I-6) | 250 | 63 |
| 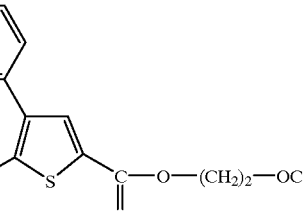<br>(I-5) | 250 | 63 |

Example B

Pyrenophora teres-Test (barley)/curative

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent

TABLE B-continued

Pyrenophora teres-Test (barley)/curative

| Active compound | Application rate of active compound in g/ha | Efficacy in % |
|---|---|---|
| 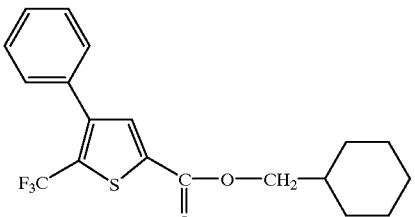 (I-26) | 250 | 61 |

We claim:

1. A microbicidal composition comprising a microbicidally effective amount of a thiophene-2-carboxylic acid derivative of the formula

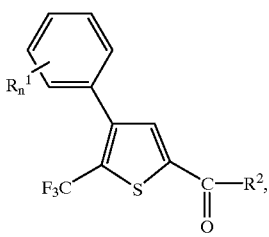 (I)

in which
R$^1$ represents halogen, cyano, nitro, alkyl, halogenoalkyl, alkoxy, halogenoalkoxy, alkylthio, halogenoalkylthio, phenyl or phenoxy,
n represents integers from 0 to 5 and
R$^2$ represents a radical of the formula

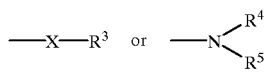

where
X represents oxygen or sulphur,
R$^3$ represents hydrogen, alkyl, alkenyl, halogenoalkyl, alkoxyalkyl, pyran-4-yl, thiopyran-4-yl, optionally substituted cycloalkyl, optionally substituted cycloalkylalkyl, optionally substituted phenyl or optionally substituted phenylalkyl, and
R$^4$ and R$^5$ independently of one another represent hydrogen, alkyl, halogenoalkyl, alkoxyalkyl, alkenyl, alkinyl, alkoxycarbonylalkyl, optionally substituted cycloalkyl, optionally substituted cycloalkenyl, optionally substituted cycloalkylalkyl, optionally substituted phenyl, optionally substituted phenylalkyl or optionally substituted heterocyclyl or
R$^4$ and R$^5$ together represent divalent alkanediyl having 4 to 6 carbon atoms or together represent a radical of the formula —(CH$_2$)$_2$—Y—(CH$_2$)$_2$—
where
Y represents oxygen, sulphur or N—R$^6$ where R$^6$ represents hydrogen, alkyl having 1 to 6 carbon atoms or benzyl,
in admixture with a diluent and/or surface-active agent.

2. Method of controlling undesired microorganisms, comprising the step of applying thiophene-2-carboxylic acid derivatives of the formula (I) according to claim 1 to the microorganisms and/or their environment.

3. Process for the preparation of microbicidal compositions, comprising the step of mixing thiophene-2-carboxylic acid derivatives of the formula (I) according to claim 1 with extenders and/or surfactants.

4. Thiophene-2-carboxylic acid derivatives of the formula

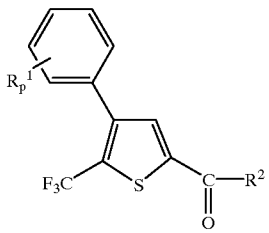 (I-a)

in which
R$^1$ represents halogen, cyano, nitro, alkyl, halogenoalkyl, alkoxy, halogenoalkoxy, alkylthio, halogenoalkylthio, phenyl or phenoxy,
p represents integers from 1 to 5 and
R$^2$ represents a radical of the formula

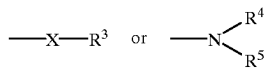

where
X represents oxygen or sulphur,
R$^3$ represents hydrogen, alkyl, alkenyl, halogenoalkyl, alkoxyalkyl, pyran-4-yl, thiopyran-4-yl, optionally substituted cycloalkyl, optionally substituted cycloalkylalkyl, optionally substituted phenyl or optionally substituted phenylalkyl, and
R$^4$ and R$^5$ independently of one another represent hydrogen, alkyl, halogenoalkyl, alkoxyalkyl, alkenyl, alkinyl, alkoxycarbonylalkyl, optionally substituted cycloalkyl, optionally substituted cycloalkenyl, optionally substituted cycloalkylalkyl, optionally substituted phenyl, optionally substitued phenylalkyl or optionally substituted heterocyclyl or $R^4$ and $R^5$ together represent divalent alkanediyl having 4 to 6 carbon atoms or together represent a radical of the formula —$(CH_2)_2$—Y—$(CH_2)_2$— where
Y represents oxygen, sulphur or N—$R^6$ where
$R^6$ represents hydrogen, alkyl having 1 to 6 carbon atoms or benzyl.

5. Process for the preparation of thiophene-2-carboxylic acid derivatives of the formula (I-a) according to claim 4, characterized in that a) thiophene-2-carboxylic acid chloride derivatives of the formula

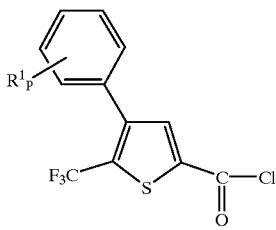

(II)

in which
$R^1$ and p have the abovementioned meanings,
are reacted either
α) with compounds of the formula

 H—X—$R^3$ (III)

in which
$R^3$ and X have the abovementioned meanings,
if appropriate in the presence of an acid binder and if appropriate in the presence of a diluent,
or
β) with amines of the formula

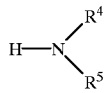

(IV)

in which
$R^4$ and $R^5$ have the abovementioned meanings, if appropriate in the presence of an acid binder and if appropriate in the presence of a diluent.

6. Composition according to claim 1, characterized in that it comprises the thiphene-2-carboxylic acid derivative of the formula

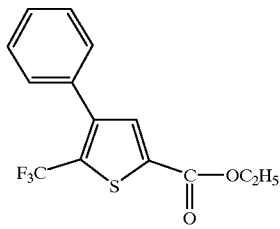

7. Thiophene-2-carboxylic acid derivative according to claim 4, comprising the formula

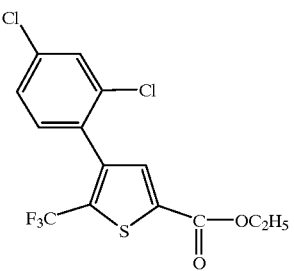

8. Thiophene-2-carboxylic acid derivatives according to claim 4, comprising the formula

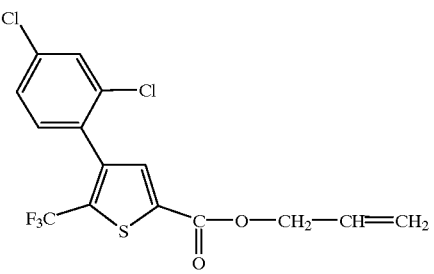

* * * * *